(12) United States Patent
Tsujimura et al.

(10) Patent No.: US 8,309,026 B2
(45) Date of Patent: Nov. 13, 2012

(54) SPECIMEN PREPROCESSING SYSTEM

(75) Inventors: Naoto Tsujimura, Hitachinaka (JP);
Nobuo Suzuki, Hitachinaka (JP);
Katsushi Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 778 days.

(21) Appl. No.: 12/180,798

(22) Filed: Jul. 28, 2008

(65) Prior Publication Data
US 2009/0035185 A1    Feb. 5, 2009

(30) Foreign Application Priority Data

Jul. 31, 2007    (JP) .................................. 2007-198271

(51) Int. Cl.
*G01N 21/00*    (2006.01)

(52) U.S. Cl. ................ 422/65; 422/62; 422/63; 422/50; 422/500; 436/180

(58) Field of Classification Search .......... 422/500–503, 422/62–65, 50; 436/180
See application file for complete search history.

(56) References Cited

U.S. PATENT DOCUMENTS 5,171,979 A * 12/1992 Kwa et al. ................. 250/223 B

FOREIGN PATENT DOCUMENTS

| JP | 2001-318104 | 11/2001 |
|---|---|---|
| JP | 3120179 | 3/2006 |
| JP | 2007-078363 | 3/2007 |
| JP | 2007-085967 A | 4/2007 |

* cited by examiner

*Primary Examiner* — Jyoti Nagpaul
(74) *Attorney, Agent, or Firm* — Mattingly & Malur, PC

(57) ABSTRACT

A specimen preprocessing system includes a determination section for determining with respect to a height of a specimen container; a specimen container lifting mechanism for lifting an opening portion of the specimen container held in a specimen rack to a same predetermined level based on determination information data of the determination section; and a plug opening mechanism for opening a plug of the specimen container lifted to the same predetermined level by the specimen container lifting mechanism.

13 Claims, 3 Drawing Sheets

STATE WHERE SPECIMEN CONTAINERS ARE MOUNTED (EXAMPLE 1)

STATE WHERE SPECIMEN CONTAINERS ARE MOUNTED (EXAMPLE 2)

SPECIMEN PREPROCESSING SYSTEM

BACKGROUND OF THE INVENTION

1. Field of the Invention

The present invention relates to a specimen preprocessing system which automatically preprocesses live body samples such as blood and urine so as to be subjected to analytical processing, and more particularly to a specimen preprocessing system provided with a plug opening unit for opening a plug of a specimen container.

2. Description of the Related Art

A specimen rack is generally structured to support approximately one to five specimen containers. The specimen container is filled with the specimen such as blood or urine collected from a subject and sealed with a plug to prevent spill of the specimen. The specimen preprocessing system is provided with a plug opening unit for opening the plug and a plug closing unit for closing the plug again for performing the specimen dispensing. Meanwhile, the specimen container may be of various types each having different height, configuration and plug configuration. The aforementioned generally employed plug opening unit requires the specimen containers of the same type (height, configuration, and plug configuration) to be mounted in the same rack.

The user is required to confirm the type of the specimen containers to be mounted in the rack, thus putting a certain strain on the user. Inappropriate mounting of the containers in the rack may result in an error causing time loss due to reconfirmation, and delay in the time from the subsequent step to the inspection report.

The type of the specimen container with the plug to be mounted in the specimen rack is limited, thus deteriorating the system flexibility.

Japanese Unexamined Patent Application Publication No. 2001-318104 discloses a rack with a mechanism for adjusting the height of the member for supporting each bottom of the specimen containers for the purpose of leveling the specimen containers.

The disclosed process, however, requires the inspecting engineer to adjust the height of the support member for supporting each bottom of the containers so as to level the specimen containers, which is hardly different from the process for distributing the specimen containers to be leveled for each rack.

SUMMARY OF THE INVENTION

It is an object of the present invention to provide a specimen preprocessing system with a plug opening unit which is capable of opening the plug even if specimen containers each having a different height (plug configuration and diameter) are mounted in the same specimen rack.

The present invention is structured for the purpose of achieving the aforementioned object.

In one aspect of the present invention, there is provided a specimen preprocessing system which includes a determination section for determining with respect to a height of a specimen container, a specimen container lifting mechanism for lifting an opening portion of the specimen container held in a specimen rack to a same predetermined level based on determination information data of the determination section, and a plug opening mechanism for opening a plug of the specimen container lifted to the same predetermined level by the specimen container lifting mechanism. The diameter and height of the specimen container may be set to arbitrary values so long as it is formed as a test-tube-like blood collecting tube. An arbitrary type of the plug may be formed, for example, as a cylindrical rubber type, plastic type and the like so long as it prevents spill of the stored specimen. The carrier line may be of any type so long as the specimen rack is carried to the processing unit. For example, the belt conveyor type, the nail push/pull type, and the robot arm type for carriage in the air may be generally employed.

The user does not have to confirm the type of the specimen container to be mounted in the rack, thus lightening up the burden of the user.

A plurality of the specimen containers may be selected by the user from the wide options, thus improving the flexibility of the specimen preprocessing system.

BRIEF DESCRIPTION OF THE DRAWINGS

Embodiment(s) of the present invention will be described in detail based on the following figures, wherein.

DESCRIPTION OF THE PREFERRED EMBODIMENTS

An embodiment of the present invention will be described referring to FIGS. 1, 2A, 2B, 3A and 3B.

Figure 1:
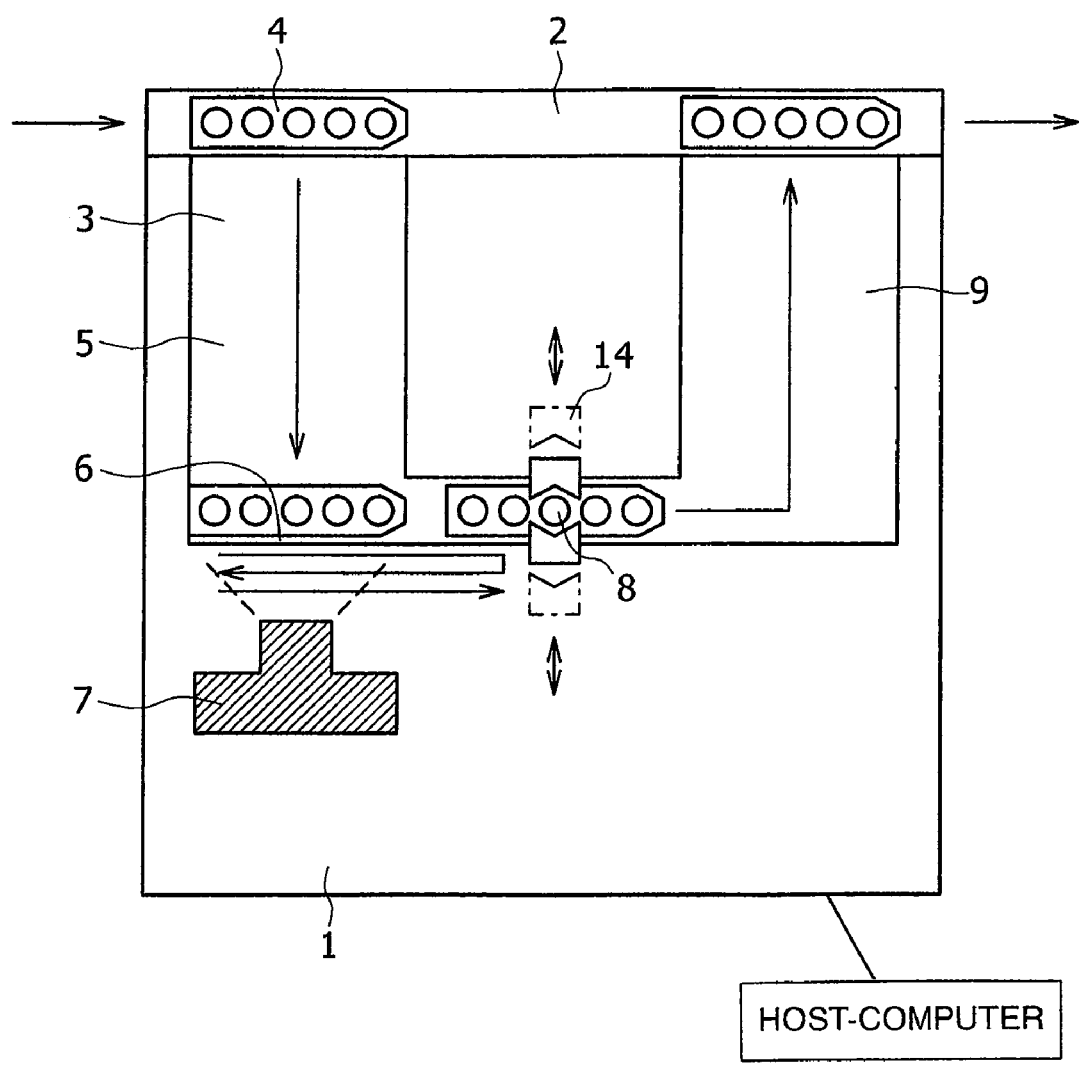
FIG. 1 is a plan view schematically showing a plug opening unit according to an embodiment of the present invention.

FIG. 1 is a plan view schematically showing a plug opening unit of a specimen preprocessing system. The plug opening unit 1 is connected to a carrier line 2 for introducing a specimen rack 4 through a specimen rack inlet 3. The introduced specimen rack 4 is carried to a determination section 6 through a buffering section 5 which is formed to prevent the specimen rack 4 sequentially carried from the carrier line 2 from being stuck. A camera 7 is installed in the determination section 6 such that the determination is made through image processing. Information with respect to the specimen container, for example, height, external diameter, and the plug configuration is preliminarily registered to be compared with the actually processed image of the specimen container so as to make the determination with respect to the height, external diameter and the plug configuration of the specimen container. As the specimen containers (one to five) mounted in each specimen rack may be subjected to an image processing simultaneously, the determination time may be markedly shorter than the time for the generally employed determination for each specimen container.

Identification numbers 13a to 13j, for example, bar codes are allocated to predetermined positions of the specimen racks 4 respectively to allow the determination with respect to the identification number of the rack simultaneously with the image processing.

Identification numbers 11a to 11j, for example, barcodes are also allocated to respective specimen containers 10a to 10j, which allow determination with respect to the identification numbers of the specimen containers through the image processing.

The determination section determines with respect to the height and the external diameter of the specimen container, the plug configuration, the presence/absence of the plug, the identification number of the specimen container, and the identification of the specimen rack to determine with respect to the operation for opening the respective specimen containers.

After performing the determination with respect to the height, the external diameter, the plug configuration, the presence/absence of the plug, the identification number of the specimen container, and the identification of the specimen rack, when the result becomes indeterminable, the error is reported to a host-computer, and the failure specimen rack or the failure specimen container will be carried to a plug opening unit feed section. Then it will be stored in an error specimen rack storage section disposed in the specimen preprocessing system via the carrier line 2.

The plug opening operation for the specimen rack 4 that is determined as having been provided without any plug is skipped. When all the specimen containers 10a to 10j in the specimen rack 4 are not plugged, they are carried to the conveyor line 2 through a specimen rack outlet 9 and further to another specimen preprocessing unit.

The specimen rack 4 determined as being normal is carried to a plug opening position 8, and allows a specimen container lifting mechanism 14 to grip the specimen container at a predetermined position so as to be lifted to the plug opening position for opening the plug.

Upon completion of the plug opening operation, the specimen rack 4 is carried to the determination section to allow the camera 7 to process the image again.

When the plug opening fails, the specimen rack is carried to the plug opening position 8 again by an arbitrary retry number of times for performing the plug opening operation. If the opening operation still fails in spite of the retry arbitrarily set number of times, the error is reported to the host-computer. The specimen rack determined as the error is stored in the error specimen rack storage section disposed in the specimen preprocessing system.

If the opening operation ends successfully, the rack is carried to the carrier line 2 through the specimen rack outlet 9 of the plug opening unit and further to another specimen preprocessing unit.

Figure 2A:
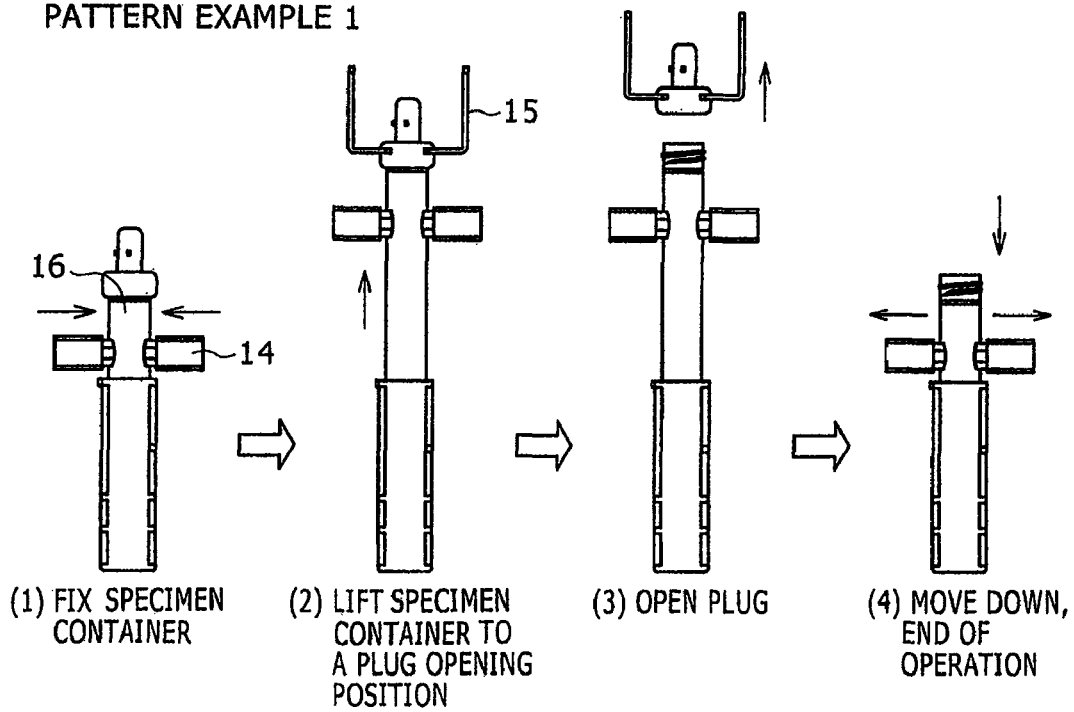
FIGS. 2A and 2B show operation patterns of the specimen container lifting mechanism and the plug opening mechanism in the plug opening position according to the embodiment of the present invention.
Figure 2B:
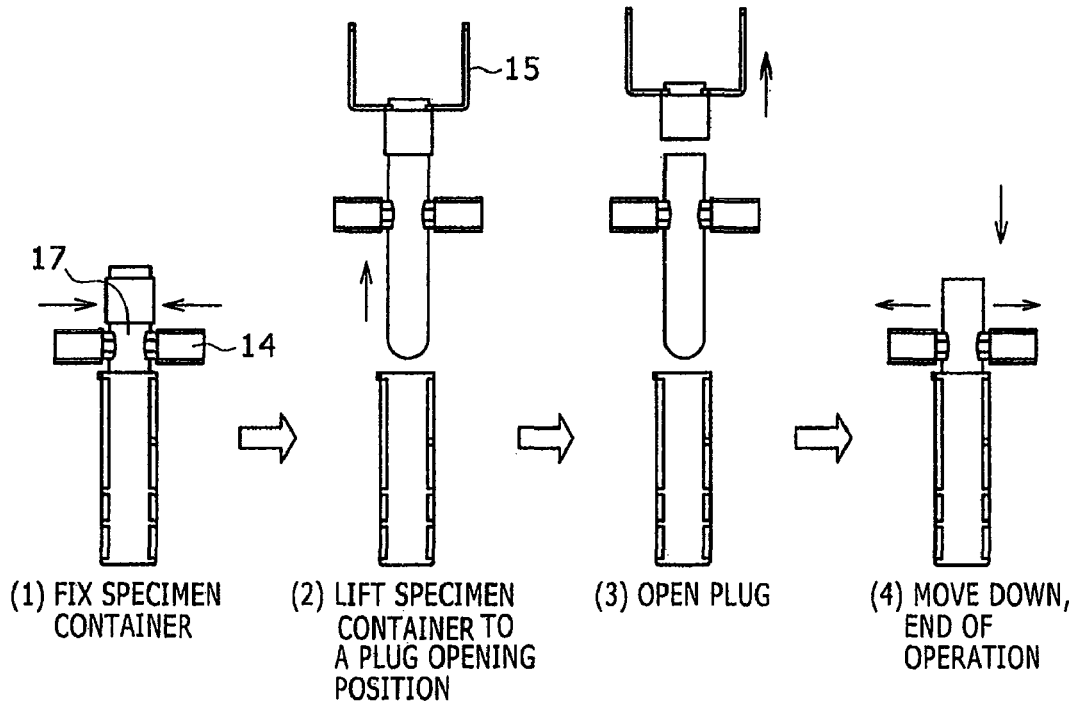

The flow of the processes of the specimen container lifting mechanism and the plug opening mechanism in the plug opening position 8 will be described referring to FIGS. 2A and 2B.

The specimen container lifting mechanism 14 has the stroke for lifting the specimen container 16 different from the one for lifting the specimen container 17 depending on the result of the determination section 6. The position of the plug opening mechanism is always kept constant. The plug opening operation is simplified by making the lifting stroke variable.

Figure 3A:
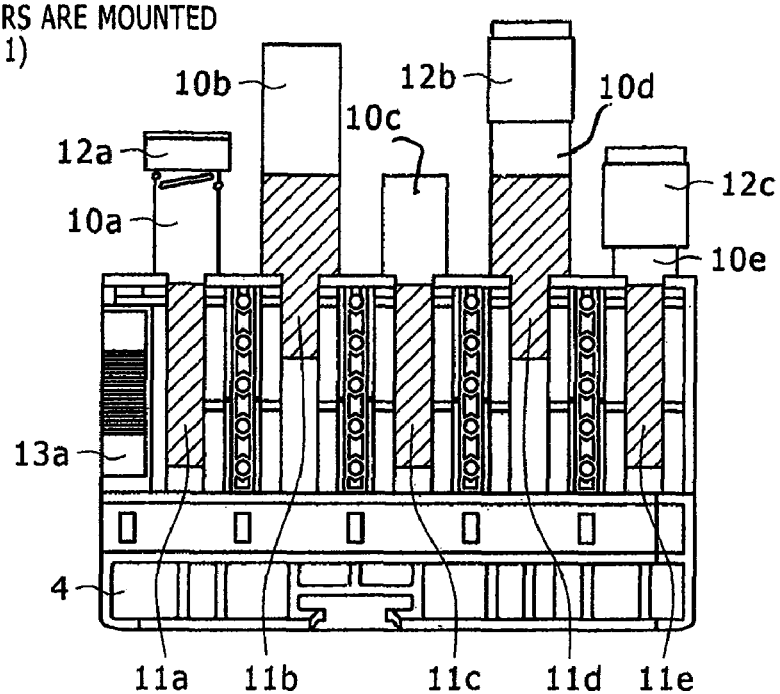
FIGS. 3A and 3B show exemplary states where the specimen containers are mounted in the specimen rack.
Figure 3B:
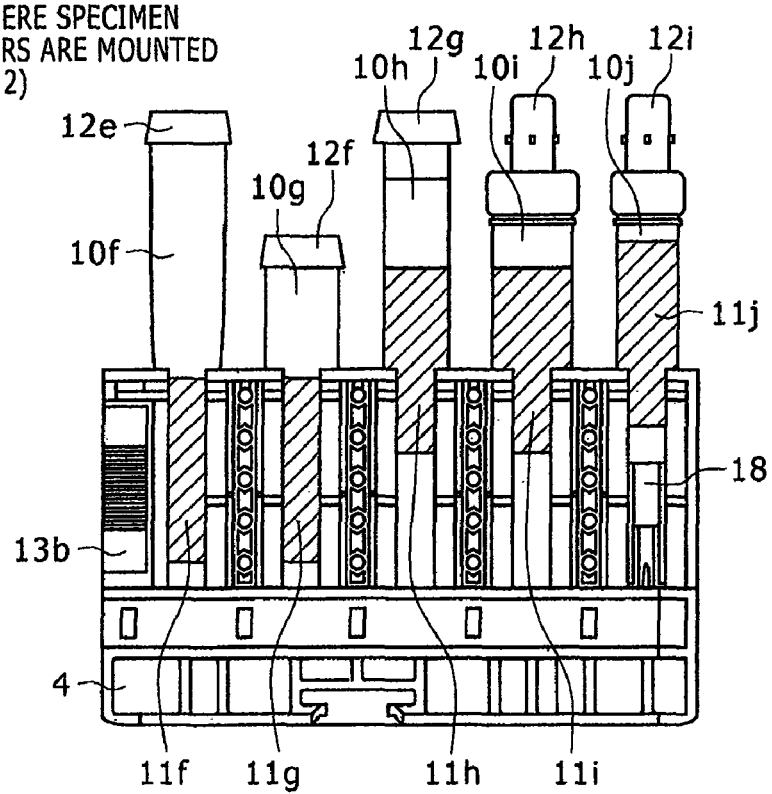

FIGS. 3A and 3B show the state where the specimen containers 10a to 10j each having different height, external diameter and plug configuration are mounted in the specimen rack 4. FIG. 3A shows plugs 12a, 12b and 12c and FIG. 3B shows plugs 12e-12i. The identification numbers 13a, 13b are allocated to predetermined positions of the specimen racks 4, the identification numbers are also allocated to the respective specimen containers 10a to 10j. The determination section 6 performs the image processing in the aforementioned state to determine the identification numbers of the specimen rack 4 and the specimen containers, respectively, so as to determine with respect to the height, the plug configuration and the external diameter of the respective specimen containers. A height adjustment spacer 18 is disposed at the lower portion of the specimen container. The image processing may be performed to determine with respect to the spacer 18 so as to accurately determine with respect to the specimen containers each with similar height. If the specimen container has a special configuration such as the specimen container 10f, the specimen container lifting mechanism 14 sets the grip position of the specimen container above the general level to avoid a plug opening operation failure owing to unstable grip at the tapered portion.

It should be understood by those skilled in the art that various modifications, combinations, sub-combinations and alterations may occur depending on design requirements and other factors insofar as they are within the scope of the appended claims or the equivalents thereof.

What is claimed is:

1. A specimen preprocessing system comprising:
a determination section to determine a height of a specimen container;
a specimen container lifting mechanism to lift an opening portion of each of one or more specimen containers from a specimen rack to a plug opening position and positioning a plug of each specimen container at a predetermined level from the specimen rack based on determination information data of the determination section; and
a plug opening mechanism to open the plug of the specimen container lifted to the predetermined level by the specimen container lifting mechanism,
wherein the one or more specimen containers have different heights and the predetermined level is the same for each of the one or more specimen containers held on the specimen rack.

2. The specimen preprocessing system according to claim 1, wherein the determination section determines an external diameter of the specimen container.

3. The specimen preprocessing system according to claim 1, wherein the determination section determines a configuration of the plug.

4. The specimen preprocessing system according to claim 1, wherein the determination section performs an image processing of the specimen rack, in which a plurality of specimen containers are mounted at a time, to generate a processed image to be compared with preliminarily registered information data to determine a height and a diameter of the specimen container, a configuration of the plug, and a presence/absence of the plug.

5. The specimen preprocessing system according to claim 1, wherein the determination section skips a plug opening operation for a specimen container that is determined as having no plug.

6. The specimen preprocessing system according to claim 4, wherein when a result of a comparison between the processed image and preliminarily registered information data becomes mismatched, the determination section determines the processed image of the specimen rack as an error so that the specimen rack is carried to an error specimen storage section in the specimen preprocessing system.

7. The specimen preprocessing system according to claim 1, wherein the determination section performs an image processing again after performing a plug opening operation using the plug opening mechanism to allow a confirmation with respect to a success or failure of the plug opening operation.

8. The specimen preprocessing system according to claim 1, wherein:
the determination section performs an image processing again after performing a plug opening operation using the plug opening mechanism, and retries the plug opening operation a predetermined number of times when the plug opening operation fails; and when all the plug opening operations performed the predetermined number of times fail, the specimen rack subjected to the determination is carried to an error specimen storage section in the specimen preprocessing system as an error specimen rack which fails the opening plug operation.

9. The specimen preprocessing system according to claim 1, wherein the determination section determines with respect to an identification number allocated to each of the specimen racks, and an identification number allocated to the specimen container mounted in the specimen rack, and reports a plug opening result to a host computer connected via a communication cable.

10. The specimen preprocessing system according to claim 1, wherein the specimen container lifting mechanism is structured to lift an appropriate one of the specimen containers in accordance with a determination result of the determination section.

11. The specimen preprocessing system according to claim 1, wherein the specimen container lifting mechanism is structured to change a position for gripping an appropriate one of the specimen containers in accordance with a determination result of the determination section.

12. The specimen preprocessing system according to claim 1, wherein the specimen container lifting mechanism is structured to change a force for gripping the specimen container even if each of the specimen containers has a different external diameter in accordance with a determination result of the determination section.

13. A specimen preprocessing system comprising:
a plurality of specimen containers:
a specimen rack configured to hold the plurality of specimen containers;
a determination section to determine a first height of a first specimen container and a second height of a second specimen container of said plurality of specimen containers, the first height being different from the second height;
a specimen container lifting mechanism to lift opening portions of the first and second specimen containers to a plug opening position from the specimen rack, wherein the specimen container lifting mechanism lifts the first specimen container a first distance to the plug opening position and the second specimen container a second distance, that is different from the first distance, to the plug opening position based on the first and second heights determined by the determination section; and
a plug opening mechanism to open a first plug of the first specimen container and a second plug of the second specimen container, respectively, after each is lifted by the specimen container lifting mechanism to the plug opening position from the specimen rack.

* * * * *